(12) United States Patent
Kataoka et al.

(10) Patent No.: US 12,196,697 B2
(45) Date of Patent: Jan. 14, 2025

(54) INSPECTION APPARATUS AND CONDUCTIVITY METER

(71) Applicant: SHIMADZU CORPORATION, Kyoto (JP)

(72) Inventors: Tatsuya Kataoka, Kyoto (JP); Yuki Yamauchi, Kyoto (JP); Masahito Yahata, Kyoto (JP); Yuichi Masuda, Kyoto (JP); Nobuhiro Namikawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 103 days.

(21) Appl. No.: 18/041,951

(22) PCT Filed: May 6, 2021

(86) PCT No.: PCT/JP2021/017326
§ 371 (c)(1),
(2) Date: Feb. 16, 2023

(87) PCT Pub. No.: WO2022/038839
PCT Pub. Date: Feb. 24, 2022

(65) Prior Publication Data
US 2023/0314356 A1   Oct. 5, 2023

(30) Foreign Application Priority Data
Aug. 20, 2020  (JP) .................................. 2020-139350

(51) Int. Cl.
*G01N 27/07*  (2006.01)
(52) U.S. Cl.
CPC .................................. *G01N 27/07* (2013.01)

(58) Field of Classification Search
CPC ..... G01N 27/06; G01N 27/07; G01N 33/1846
See application file for complete search history.

(56) References Cited

U.S. PATENT DOCUMENTS 3,991,623 A * 11/1976 Murdock ............... G01N 27/06
73/170.34
4,626,413 A * 12/1986 Blades ............... G01N 33/1846
422/78

(Continued)

FOREIGN PATENT DOCUMENTS

JP          6556699 B2     8/2019

OTHER PUBLICATIONS

International Search Report for PCT/JP2021/017326 dated Jul. 20, 2021.

(Continued)

*Primary Examiner* — Jay Patidar
(74) *Attorney, Agent, or Firm* — Sughrue Mion, PLLC

(57) ABSTRACT

A conductivity meter includes a measurement unit including an electrode arranged as being in contact with sample water and a substrate on which a circuit that processes information outputted from the measurement unit is mounted. The measurement unit and the substrate are connected to each other, with a wall portion being interposed, the wall portion partitioning a space in a housing into a water section and an electric section. The measurement unit is arranged on a first surface of the wall portion on a side of the water section such that the electrode is located in an opening provided in the wall portion. The substrate is arranged on a second surface of the wall portion on a side of the electric section such that an electrode contact that electrically connects a power supply and a circuit to each other is located in the opening.

7 Claims, 6 Drawing Sheets

(56) References Cited

U.S. PATENT DOCUMENTS

| | | | | |
|---|---|---|---|---|
| 8,557,597 | B2 * | 10/2013 | Akechi | G01N 33/1846 422/78 |
| 10,203,287 | B2 * | 2/2019 | Clark | G01N 21/8507 |
| 11,385,194 | B2 * | 7/2022 | Yoshida | G01N 33/2888 |
| 2016/0084784 | A1 | 3/2016 | Rajagopalan et al. | |

OTHER PUBLICATIONS

Written Opinion for PCT/JP2021/017326 dated Jul. 20, 2021.
Communication dated Aug. 29, 2024 from the European Patent Office in application No. 21857991.0.

* cited by examiner

INSPECTION APPARATUS AND CONDUCTIVITY METER

CROSS REFERENCE TO RELATED APPLICATIONS

This application is a National Stage of International Application No. PCT/JP2021/017326 filed on May 6, 2021, claiming priority based on Japanese Patent Application No. 2020-139350 filed on Aug. 20, 2020.

TECHNICAL FIELD

The present disclosure relates to a conductivity meter that measures a conductive property of sample water and an inspection apparatus including the conductivity meter.

BACKGROUND ART

A conductive property of sample water may be measured as an indicator that indicates a property of sample water. The conductive property of sample water is an indicator that indicates a ratio of an electrolyte dissolved in sample water, and used, for example, for measuring an amount of total organic carbon (TOC) in sample water. Specifically, a decomposed product resulting from oxidation of an organic substance in sample water varies the conductive property of sample water, and hence the decomposed product can be detected measurement of the conductive property of sample water and the amount of TOC can be measured by detection of the decomposed product.

Japanese Patent No. 6556699 (PTL 1) discloses a device for measuring the conductive property of a liquid, which comprises a measuring chamber for containing a sampling volume to be irradiated with UV rays and a UV-transparent window being located between the measuring chamber and a source of UV rays, hermetically closing a first side of the measuring chamber. According to the disclosure in PTL 1, two measuring electrodes are etched intended as being in contact with the liquid present in the measuring chamber. PTL 1 describes connection of an electrode which is a measurement electrode to a computer via a cable.

CITATION LIST

Patent Literature

PTL 1: Japanese Patent No. 6556699

SUMMARY OF INVENTION

Technical Problem

A circuit that processes a detection value from an electrode should be protected so as not to be in contact with a liquid. As a method of protecting the circuit against the liquid, as in the device described in PTL 1 where the electrode and the computer are connected to each other through the cable, for example, a method of connecting the electrode and the circuit to each other through a cable to locate the circuit away from an area where a liquid such as sample water is handled is available. With a longer length of the cable through which the electrode and the circuit are connected to each other, however, noise is superimposed on the detection value as being affected by a parasitic capacitance. Therefore, connection of the electrode and the circuit to each other through the cable leads to lowering in accuracy of a conductivity meter.

By bringing the electrode and the circuit closer to each other, accuracy of the conductivity meter can be enhanced, however, contact of the circuit with the liquid is more likely.

One object of the present disclosure is to enhance accuracy of a conductivity meter provided in an inspection apparatus that inspects sample water and to protect an electric system in the inspection apparatus.

Solution to Problem

An inspection apparatus in the present disclosure is an inspection apparatus that inspects sample water, and includes a housing, a wall portion that partitions a space in the housing into a first section and a second section, the wall portion being provided with an opening, a conductivity meter that measures a conductive property of sample water, and a flow-in tube through which sample water flows into the conductivity meter. The conductivity meter includes a measurement unit including an electrode portion arranged as being in contact with sample water and a substrate on which a circuit is mounted, the circuit processing information outputted from the measurement unit. The measurement unit and the substrate are connected to each other with the wall portion being interposed. The measurement unit is arranged on a first surface of the wall portion on a side of the first section such that the electrode portion is located in the opening. The substrate is arranged on a second surface of the wall portion on a side of the second section such at a contact that electrically connects the electrode portion and the circuit to each other is located in the opening.

A conductivity meter in the present disclosure is a conductivity meter that measures a conductive property of sample water, and includes a measurement unit including an electrode portion arranged as being in contact with sample water and a substrate on which a circuit is mounted, the circuit processing information outputted from the measurement unit. The measurement unit and the substrate are connected to each other with a wall portion being interposed, the wall portion partitioning a space in a housing into a first section and a second section. The measurement unit is arranged on a first surface of the wall portion on a side of the first section such that the electrode portion is located in an opening provided in the wall portion. The substrate is arranged on a second surface of the wall portion on a side of the second section such that a contact that electrically connects the electrode portion and the circuit to each other is located in the opening.

Advantageous Effects of Invention

According to the present disclosure, since a substrate is arranged in the second section partitioned by the wall portion from the first section where the measurement unit including the electrode portion arranged as being in contact with sample water is arranged, the substrate can be protected against sample water. Furthermore, since the electrode portion and the contact of the substrate are connected to each other through the opening in the wall portion, a distance from the electrode portion to the circuit can be shorter, and consequently, information outputted from the measurement unit can be sent to the circuit without noise being superimposed thereon.

DESCRIPTION OF EMBODIMENTS

Figure 1:
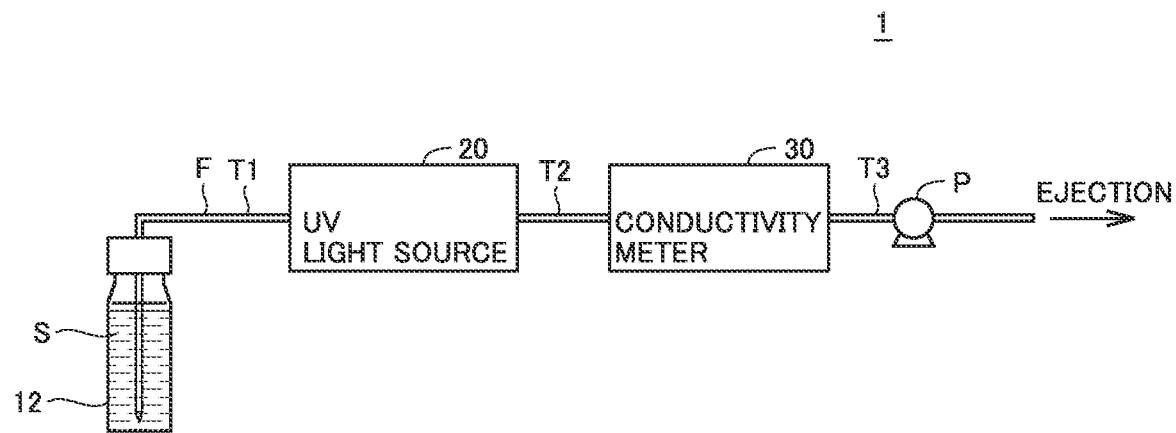
FIG. 1 is a schematic diagram for illustrating an overall configuration of an inspection apparatus 1.

An embodiment of the present disclosure will be described in detail below with reference to the drawings. The same or corresponding elements in the drawings have the same reference characters allotted and description thereof will not be repeated.

<Overall Configuration of Inspection Apparatus 1>

FIG. 1 is a schematic diagram for illustrating an overall configuration of an inspection apparatus 1. Inspection apparatus 1 is an apparatus that measures an amount of TOC (a concentration of TOC) in sample water. Inspection apparatus 1 is what is called a wet oxidation inspection apparatus that oxidizes an organic substance in sample water by emission of ultraviolet rays to sample water.

Referring to FIG. 1, inspection apparatus 1 draws sample water S in a vial 12 into a flow channel F by means of a pump P. On flow channel F, a UV light source 20 and a conductivity meter 30 are arranged.

Though not shown, UV light source 20 is a double-wall excimer lamp that includes an inner tube in which sample water S passes through an interior space and an outer tube arranged on an outer circumference of the inner tube at a distance therefrom, and emits ultraviolet rays from discharge gas sealed in a discharge space between the outer tube and the inner tube to the interior space in the inner tube. By emission of ultraviolet rays to sample water S that passes through the interior space in UV light source 20, an organic substance in sample water S is oxidized.

Vial 12 and the inner tube (on an upstream side) of UV light source 20 are connected to each other through a tube T1 that defines flow channel F. On a downstream side of the inner tube of UV light source 20, a tube T2 is connected. The inner tube can also be said as a part of flow channel F.

Conductivity meter 30 includes a flow channel that can be connected to tube T2. A tube T3 is connected on the downstream side of the flow channel provided in conductivity meter 30, and sample water S that has passed through conductivity meter 30 is ejected through tube T3.

When an organic substance in sample water S is oxidized by ultraviolet rays, it is finally decomposed into water and carbon dioxide. As carbon dioxide which is the decomposed product is dissolved in water, ions are produced and the conductivity of sample water S varies. Conductivity meter 30 can detect the decomposed product in sample water S by measuring the conductivity varied by carbon dioxide which is the decomposed product.

Figure 2:
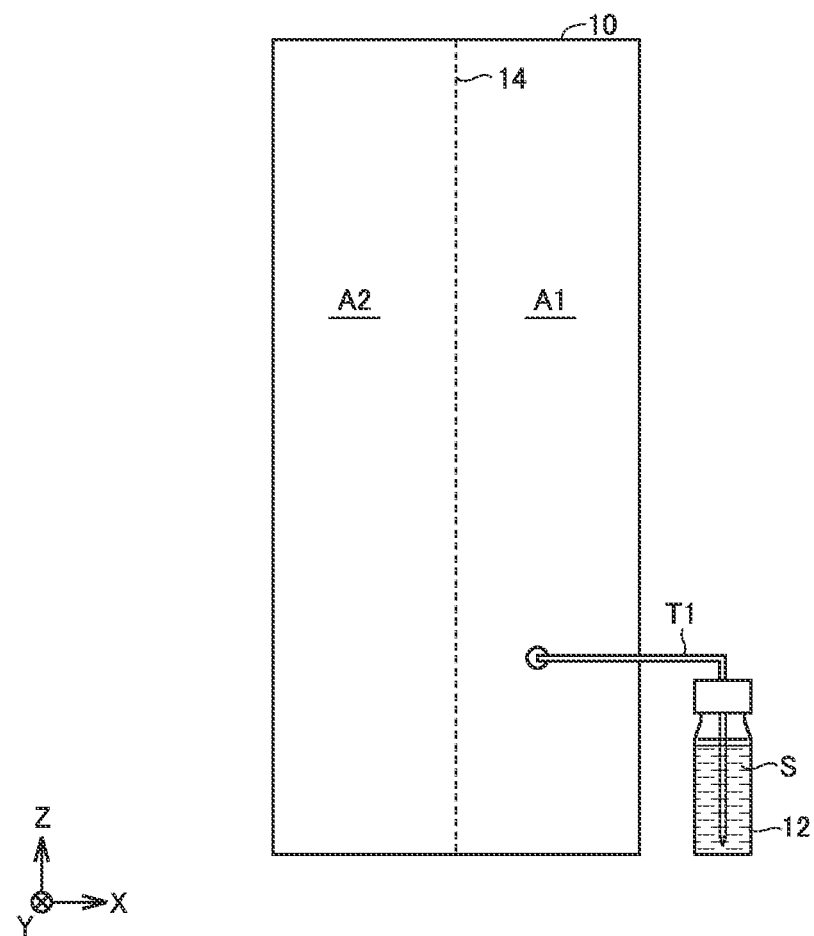
FIG. 2 is a schematic diagram showing an overall structure of a housing 10 of inspection apparatus 1.

FIG. 2 is a schematic diagram showing an overall structure of a housing 10 of inspection apparatus 1. Tube T1 for connection to vial 12 extends from housing 10 of inspection apparatus 1. UV light source 20, conductivity meter 30, and pump P described with reference to FIG. 1 are arranged in housing 10. A manner of arrangement will be described later.

A wall portion 14 partitions a space in housing 10 into a water section A1 where sample water S is handled and an electric section A2 where sample water S is not handled. For example, flow channel F is arranged in water section A1. On the other hand, an apparatus to be protected against water is arranged in electric section A2. For example, a substrate on which a circuit is mounted, an electric system, or the like is arranged in electric section A2.

As shown in FIG. 2, since wall portion 14 partitions the space in housing 10 of inspection apparatus 1 according to the present embodiment into water section A1 and electric section A2, a substrate on which a circuit is mounted can be protected against water and data can be protected.

A plane of wall portion 14 is defined as a Y-Z plane and an axis orthogonal to each of a Y axis and a Z axis is defined as an X axis.

<Water Section A1>

Figure 3:
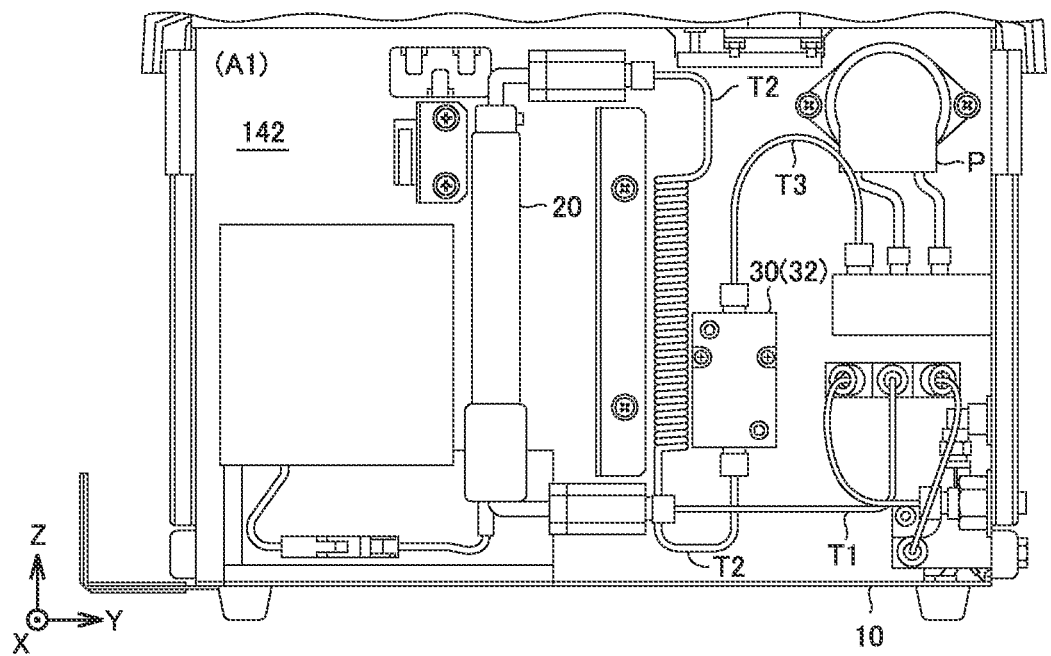
FIG. 3 is a schematic diagram showing a first surface 142 of a wall portion 14 on a side of a water section A1.

An apparatus arranged in water section A1 will be described. FIG. 3 is a schematic diagram showing a first surface 142 of wall portion 14 on a side of water section A1. UV light source 20, pump P, and a measurement unit 32 of conductivity meter 30 are attached to first surface 142 in housing 10. Apparatuses attached to first surface 142 are connected to one another through tubes.

Tube T1 is connected to an upstream side of UV light source 20. Though not shown, tube T1 is connected to vial 12.

Tube T2 is connected on the upstream side of UV light source 20. Tube T2 performs a function as a cooling unit. Specifically, at least a part of tube T2 is composed of a material higher in thermal conductivity than other tubes.

As an organic substance in sample water S is oxidized, oxidation heat is generated. The conductivity is varied with variation in temperature. Therefore, generated oxidation heat should be dissipated before measurement of sample water S with conductivity meter 30. As tube T2 performs also a function as a cooling unit as described above, the conductivity can highly accurately be measured.

Measurement unit 32 of conductivity meter 30 is connected to the downstream side of tube T2. Conductivity meter 30 includes measurement unit 32 including a pair of electrodes 324 (see FIG. 6) in contact with sample water S and a substrate 34 (see FIG. 4) where a circuit 342 that processes information outputted from measurement unit 32 is mounted. Circuit 342 performs, for example, processing (A/D conversion processing) for converting analog information outputted from the measurement unit into digital information. Circuit 342 may include an arithmetic circuit that performs processing for calculating a measurement value based on digital information. Measurement unit 32 is arranged on a side of water section A1 in housing 10. Substrate 34 is arranged on a side of electric section A2 within housing 10.

A flow channel is defined in the inside of measurement unit 32, and the flow channel in the inside of measurement unit 32 is connected to tube T2 and tube T3. As set forth above, a component through which sample water S passes is arranged in water section A1.

Conductivity meter 30 should only be a component that measures an indicator indicating a conductive property of sample water, and it is not limited to a component that measures a conductivity. For example, conductivity meter 30 may measure a resistivity. Though conductivity meter 30 is defined in the present embodiment as including a pair of electrodes 324 and measuring a conductivity of sample water with a two-terminal method, it may measure the conductivity of sample water with another method such as a four-probe method or a four-terminal method. In other words, conductivity meter 30 should only include an electrode portion that is arranged as being in contact with sample water an measures an indicator indicating a conductive property of sample water, and the electrode portion may be composed of two electrodes or four electrodes.

<Electric Section A2>

Figure 4:
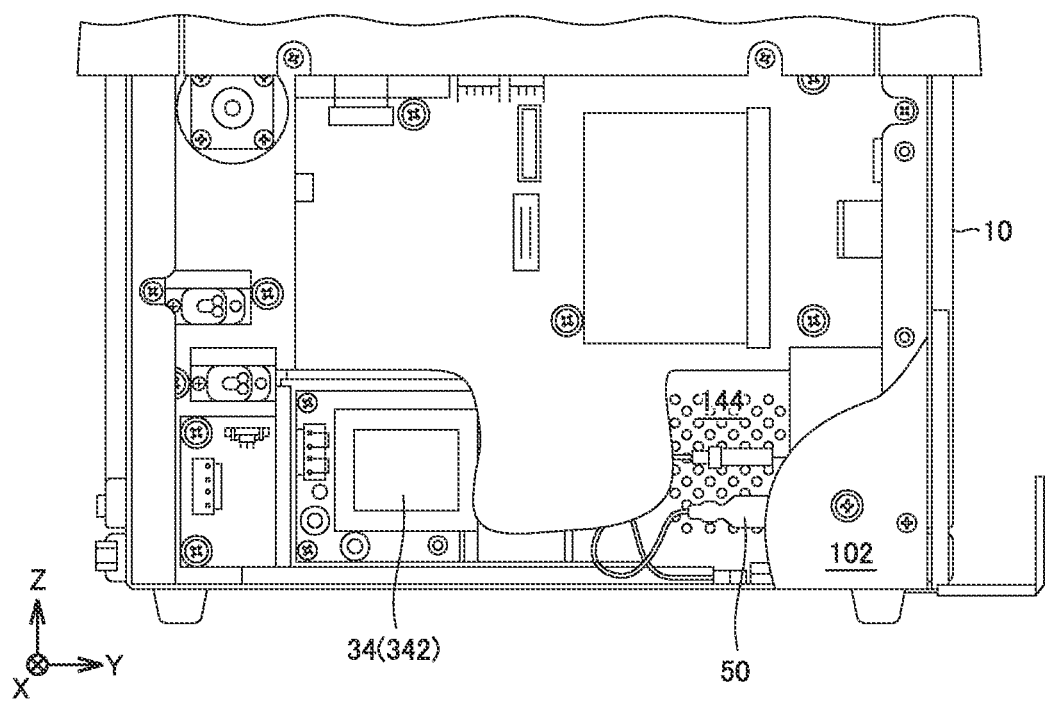
FIG. 4 is a schematic diagram showing a second surface 144 of wall portion 14 on a side of an electric section A2.

An apparatus arranged in electric section A2 will be described. FIG. 4 is a schematic diagram showing second surface 144 of wall portion 14 on the side of electric section A2. A cover 102 is attached to a rear surface of housing 10 and a wall portion is further arranged between cover 102 and wall portion 14.

Referring to FIG. 4, substrate 34 on which circuit 342 is mounted is attached to second surface 144. A power supply apparatus 50 is arranged in electric section A2.

Wetting of circuit 342 and power supply apparatus 50 with water causes a failure. In inspection apparatus 1, wall portion 14 partitions the space in housing 10 into water section A1 where sample water S is handled and electric section A2 where sample water S is not handled, and an apparatus that will fail if it is wetted with water, such as circuit 342 and power supply apparatus 50, is arranged in electric section A2. Inspection apparatus 1 that is less likely to fail can thus be provided.

<Conductivity Meter 30>

As described above, conductivity meter 30 includes measurement unit 32 arranged on the side of water section A1 and substrate 34 (see FIG. 9) arranged on the side of electric section A2. A configuration of measurement unit 32 and a method of electrical connection between measurement unit 32 and substrate 34 will be described below.

Figure 5:
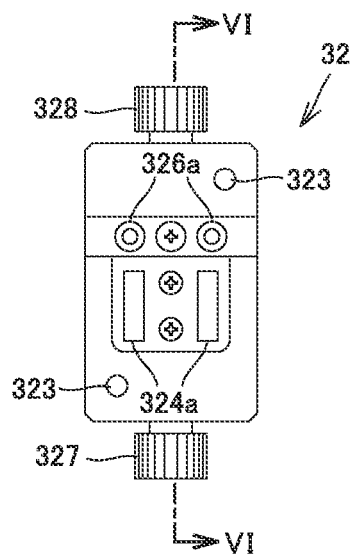
FIG. 5 is a front view of a measurement unit 32.
Figure 6:
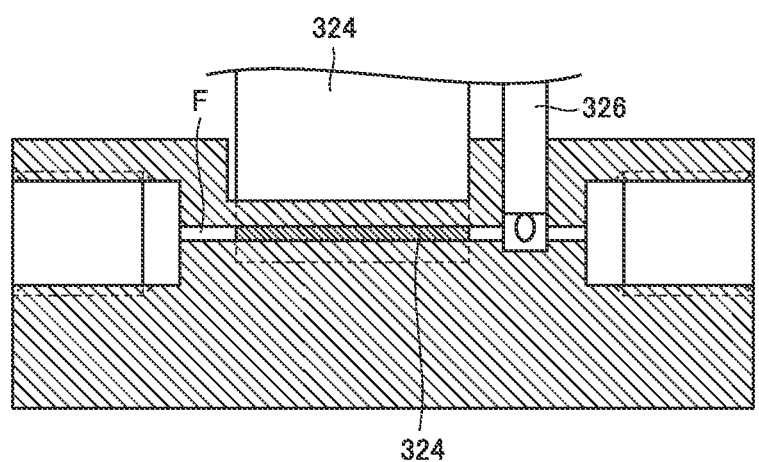
FIG. 6 is a schematic cross-sectional view along the line VI-VI in FIG. 5.

The configuration of measurement unit 32 will be described with reference to FIGS. 5 and 6. FIG. 5 is a front view of measurement unit 32. FIG. 6 is a schematic cross-sectional view along the line VI-VI in FIG. 5. The front view of measurement unit 32 shown in FIG. 5 is a view with a surface opposed to first surface 142 at the time of attachment of measurement unit 32 to first surface 142 being defined as the front surface. FIG. 6 does not show some of features such as a screw and coupling portions 327 and 328.

Referring to FIG. 5, measurement unit 32 includes two openings 323, two electrode contacts 324a, two thermistor contacts 326a, and coupling portions 327 and 328.

Figure 8:
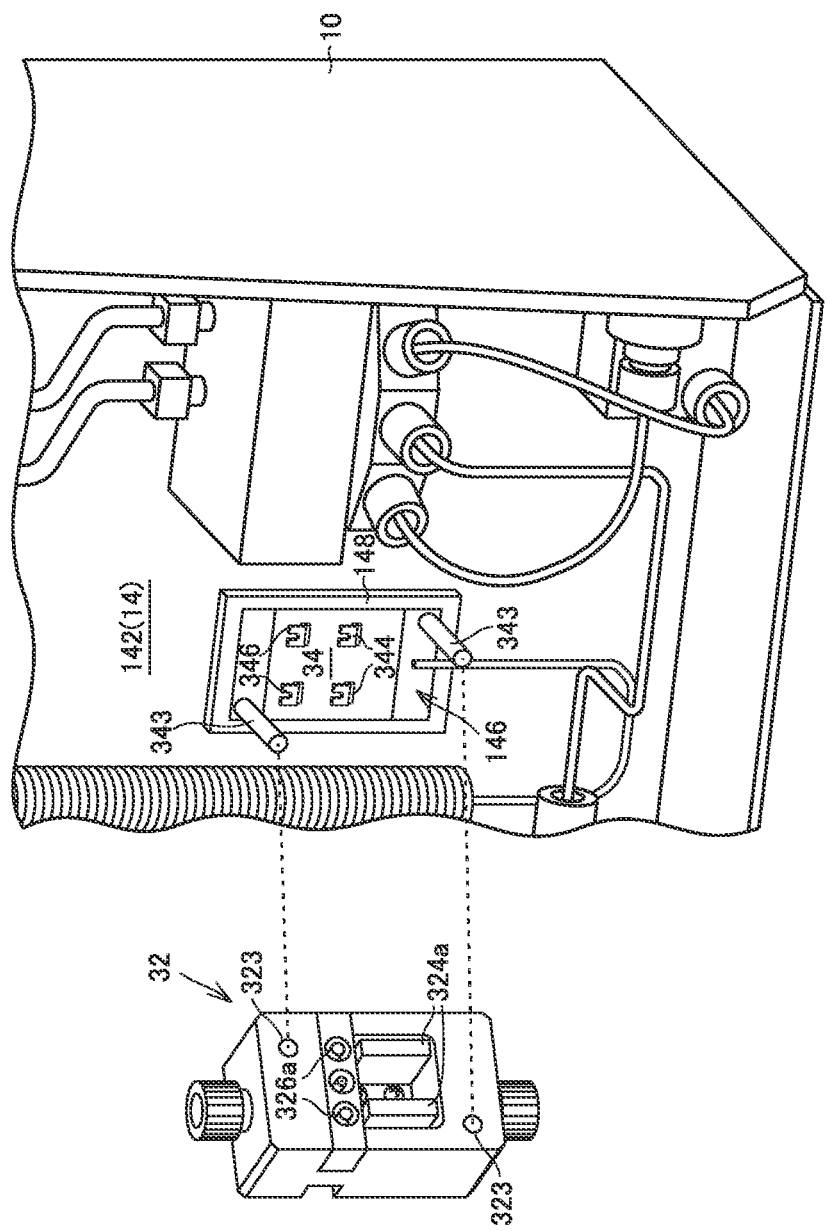
FIG. 8 is a diagram for illustrating a method of connecting measurement unit 32 and a substrate 34 to each other.

Opening 323 is shaped such that a columnar connection portion 343 provided in substrate 34 can be inserted therein (see FIG. 8). Two openings 323 are provided in the housing of measurement unit 32, and provided at positions corresponding to two respective connection portions 343 provided in substrate 34.

Electrode contact 324a is a contact of electrode 324 shown in FIG. 6. Electrode 324 is formed to penetrate flow channel F defined in measurement unit 32 as shown in FIG. 6. Consequently, when sample water S flows through flow channel F, sample water S comes in contact with at least a part of electrode 324. Though FIG. 6 shows only electrode 324 on one side, another electrode 324 is also formed to penetrate flow channel F similarly defined in measurement unit 32.

Though not shown, two thermistor contacts 326a are electrically connected to thermistor 326 shown in FIG. 6 and arranged on flow channel F defined in measurement unit 32. Thermistor 326 measures a temperature of sample water S that passes through flow channel F defined in measurement unit 32. The conductivity is affected by a temperature. Being provided with thermistor 326, conductivity meter 30 can measure the temperature of sample water S and hence can accurately measure the conductivity.

Coupling portions 327 and 328 are constructed to be connected to tube T2 and tube T3, respectively. As tube T2 and tube T3 are connected to respective coupling portions 327 and 328, sample water S flows through flow channel F in measurement unit 32.

Figure 7:
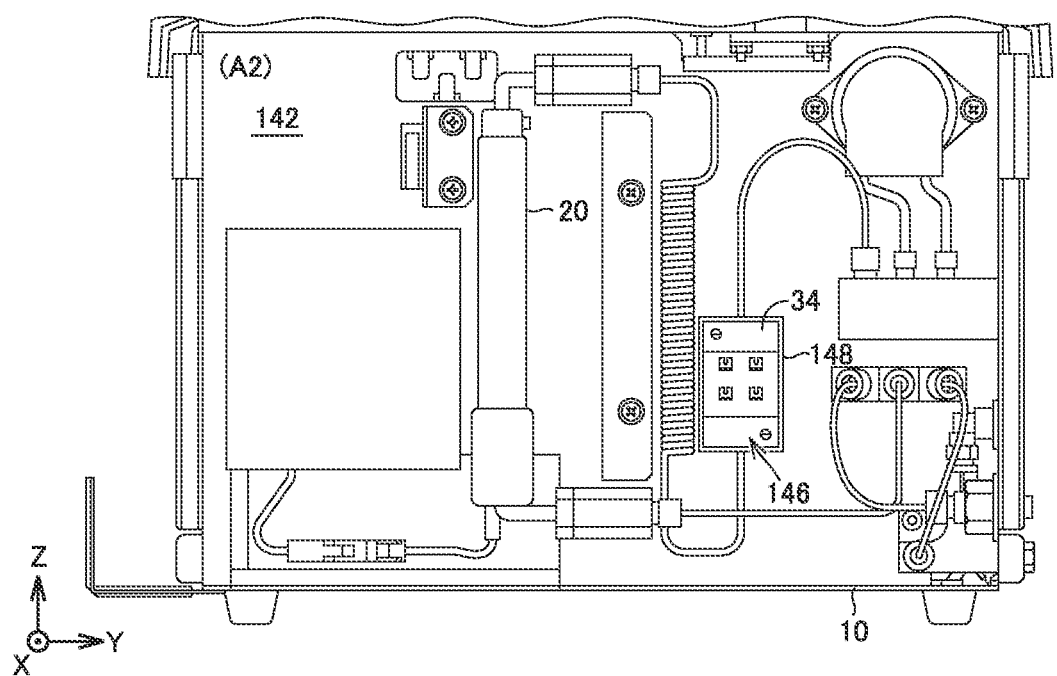
FIG. 7 is a schematic diagram showing first surface 142 with measurement unit 32 having been removed.
Figure 9:
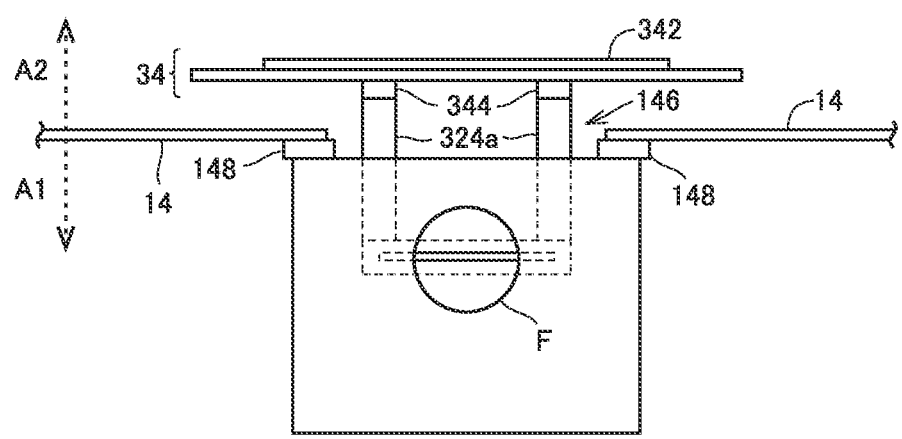
FIG. 9 is a diagram showing a state when measurement unit 32 and substrate 34 are connected to each other.

A method of connecting measurement unit 32 and substrate 34 to each other will now be described. FIG. 7 is a schematic diagram showing first surface 142 with measurement unit 32 having been removed. FIG. 8 is a diagram for illustrating a method of connecting measurement unit 32 and substrate 34 to each other. FIG. 9 is a diagram showing a state when measurement unit 32 and substrate 34 are connected to each other.

Referring to FIG. 7, an opening 146 is provided in wall portion 14. Packing 148 is provided on first surface 142 around an outer periphery of opening 146. Opening 146 is smaller than measurement unit 32 and substrate 34, and measurement unit 32 and substrate 34 are electrically connected to each other through opening 146 with wall portion 14 lying therebetween.

Substrate 34 is arranged on the side of electric section A2 as described above. Referring to FIGS. 7 and 8, substrate 34 includes a pair of electrode contacts 344 for electrical connection between electrode 324 and circuit 342, a pair of thermistor contacts 346 for electrical connection between thermistor 326 and circuit 342, and two connection portions 343.

Substrate 34 is arranged on second surface 144 such that electrode contact 344 and thermistor contact 346 are located in opening 146.

Two connection portions 343 are each a protrusion in a columnar shape. Two connection portions 343 are formed on a surface where electrode contact 344 is arranged as protruding toward water section A1 through opening 146 when substrate 34 is arranged on second surface 144.

Referring to FIG. 8, connection portion 343 is inserted in opening 323 in measurement unit 32 to connect measurement unit 32 and substrate 34 to each other when measurement unit 32 is arranged on first surface 142. In other words, opening 323 in measurement unit 32 and connection portion 343 of substrate 34 function as the connection portion that connects measurement unit 32 and substrate 34 to each other.

Referring to FIG. 9, as connection portion 343 is inserted in opening 323 to connect measurement unit 32 and substrate 34 to each other, electrode contact 324a of measurement unit 32 and electrode contact 344 of substrate 34 come in contact with each other, and consequently, electrode 324 and circuit 342 are electrically connected to each other. Though not shown, as connection portion 343 is inserted in opening 323 to connect measurement unit 32 and substrate 34 to each other, thermistor contact 326a of measurement unit 32 and thermistor contact 346 of substrate 34 come in contact with each other, and consequently, thermistor 326 and circuit 342 are electrically connected to each other. FIG. 9 does not show such features as connection portion 343 and opening 323.

Electrode contact 324a of measurement unit 32 and electrode contact 344 of substrate 34 are preferably plated with gold in order to lower a contact resistance. Similarly, thermistor contact 326a of measurement unit 32 and thermistor contact 346 of substrate 34 are preferably plated with gold in order to lower the contact resistance.

As set forth above, measurement unit 32 of conductivity meter 30 and substrate 34 are connected to each other with wall portion 14 lying therebetween, and electrode contact 324a of electrode 324 and electrode contact 344 of substrate 34 are arranged as being located in opening 146 in wall portion 14.

Therefore, electrode 324 (more exactly, electrode contact 324a) and electrode contact 344 of substrate 34 can be brought in direct contact with each other, and information (for example, analog information which represents a detection value) outputted from measurement unit 32 can be sent to circuit 342 of substrate 34 without noise being superimposed thereon. Furthermore, since electronic components such as substrate 34 are arranged in electric section A2 partitioned from water section A1 by wall portion 14, they can be protected against sample water S.

Since packing 148 is arranged between measurement unit 32 and first surface 142, entry of water through a gap between measurement unit 32 and first surface 142 toward electric section A2 can be prevented and hence waterproofness on the side of electric section A2 can be enhanced. Packing 148 should only be a seal capable of preventing entry of water through the gap between measurement unit 32 and first surface 142 toward electric section A2, and a gasket or the like may be applicable. Packing 148 should only have such a property as being resistant to a sample to be subjected to measurement by inspection apparatus 1, and it can be selected as appropriate depending on an object to be measured. Though packing 148 is defined as being arranged on first surface 142, it may be arranged in measurement unit 32.

In the embodiment, inspection apparatus 1 is defined as an apparatus that measures an amount of TOC in sample water. Conductivity meter 30 described in the present embodiment can be applied also to an inspection apparatus configured differently from inspection apparatus 1 shown in the embodiment, so long as the inspection apparatus is configured such that the conductivity meter is arranged on a flow channel where sample water (a liquid sample) flows. For example, conductivity meter 30 can be applied also to an inspection apparatus without UV light source 20.

In the embodiment, by insertion of connection portion 343 in opening 323 with wall portion 14 lying between measurement unit 32 and substrate 34, measurement unit 32 and substrate 34 are connected to each other and conductivity meter 30 is fixed to wall portion 14. In conductivity meter 30, measurement unit 32 and substrate 34 may individually be fixed to wall portion 14. A construction in which conductivity meter 30 is fixed to wall portion 14 by connection of measurement unit 32 and substrate 34 to each other is advantageous in reduction in number of components.

Aspects

The embodiment described above is understood by a person skilled in the art as specific examples of aspects below.

(Clause 1) An inspection apparatus that inspects sample water according to one aspect includes a housing, a wall portion that partitions a space in the housing into a first section and a second section, the wall portion being provided with an opening, a conductivity meter that measures a conductive property of sample water, the conductivity meter being arranged in the first section, and a flow-in tube through which sample water flows into the conductivity meter. The conductivity meter includes a measurement unit including an electrode portion arranged as being in contact with sample water and a substrate on which a circuit is mounted, the circuit processing information outputted from the measurement unit. The measurement unit and the substrate are connected to each other with the wall portion being interposed. The measurement unit is arranged on a first surface of the wall portion on a side of the first section such that the electrode portion is located in the opening. The substrate is arranged on a second surface of the wall portion on a side of the second section such that a contact that electrically connects the electrode portion and the circuit to each other is located in the opening.

According to the inspection apparatus described in Clause 1, since the substrate is arranged in the second section partitioned by the wall portion from the first section where the measurement unit including the electrode portion arranged as being in contact with sample water is arranged, the substrate can be protected against sample water. Furthermore, since the electrode portion and the contact of the substrate are connected to each other through the opening in the wall portion, a distance from the electrode portion to the circuit can be shorter, and consequently, information outputted from the measurement unit can be sent to the circuit without noise being superimposed thereon.

(Clause 2) The inspection apparatus according to Clause 1 further includes a seal arranged around an outer circumference of the opening in the first surface and between the wall portion and the measurement unit.

According to the inspection apparatus described in Clause 2, since entry of water from between the wall portion and the measurement unit toward the second section can be prevented, waterproofness on the side of the second section where the substrate is arranged can be enhanced.

(Clause 3) In the inspection apparatus according to Clause 1 or 2, a contact of the electrode portion in contact with the contact of the substrate is plated with gold.

According to the inspection apparatus described in Clause 3, since a contact resistance between the contact of the substrate and the contact of the electrode portion can be lowered, noise can be prevented from being superimposed on information outputted from the measurement unit.

(Clause 4) In the inspection apparatus according to any one of Clauses 1 to 3, the measurement unit further includes a temperature sensor that measures a temperature of sample water. A contact of the temperature sensor is arranged as being located in the opening when the measurement unit is arranged on the first surface. The contact of the substrate that electrically connects the contact of the temperature sensor and the circuit to each other is arranged as being located in the opening when the substrate is arranged on the second surface.

According to the inspection apparatus described in Clause 4, since the temperature of sample water can be measured, the conductive property affected by the temperature can more accurately be measured. Since the contact of the temperature sensor and the contact of the substrate are connected to each other through the opening in the wall portion, a distance from the temperature sensor to the circuit can be shorter, and consequently, information outputted from the temperature sensor can be sent to the circuit without noise being superimposed thereon.

(Clause 5) In the inspection apparatus according to any one of Clauses 1 to 4, the conductivity meter further includes a connection portion that connects the measurement unit and the substrate to each other.

According to the inspection apparatus described in Clause 5, the connection portion strengthens connection between the measurement unit and the substrate, so that entry of water from between the wall portion and the measurement unit toward the second section can be prevented and hence waterproofness on the side of the second section where the substrate is arranged can be enhanced. Connection of the measurement unit and the substrate to each other can allow the conductivity meter to be fixed to the wall portion, and the number of components necessary for fixing the conductivity meter to the wall portion can be reduced.

(Clause 6) A conductivity meter that measures a conductive property of sample water according to one aspect includes a measurement unit including an electrode portion arranged as being in contact with sample water and a substrate on which a circuit is mounted, the circuit processing information outputted from the measurement unit. The measurement unit and the substrate are connected to each other with a wall portion being interposed, the wall portion partitioning a space in a housing into a first section and a second section. The measurement unit is arranged on a first surface of the wall portion on a side of the first section such that the electrode portion is located in an opening provided in the wall portion. The substrate is arranged on a second surface of the wall portion on a side of the second section such that a contact that electrically connects the electrode portion and the circuit to each other is located in the opening.

According to the conductivity meter described in Clause 6, since the substrate is arranged in the second section partitioned by the wall portion from the first section where the measurement unit including the electrode portion arranged as being in contact with sample water is arranged, the substrate can be protected against sample water. Furthermore, since the electrode portion and the contact of the substrate are connected to each other through the opening in the wall portion, a distance from the electrode portion to the circuit can be shorter, and consequently, information outputted from the measurement unit can be sent to the circuit without noise being superimposed thereon.

(Clause 7) According to the conductivity meter described in Clause 6, the measurement unit is arranged on the first surface of wall portion with a seal being interposed, the seal being arranged around an outer circumference of the opening in the first surface.

According to the conductivity meter described in Clause 7, since entry of water from between the wall portion and the measurement unit toward the second section can be prevented, waterproofness on the side of the second section where the substrate is arranged can be enhanced.

The embodiment disclosed herein is also intended to be carried out as being combined as appropriate within the technically consistent scope. It should be understood that the embodiment disclosed herein is illustrative and non-restrictive in every respect. The scope of the present invention is defined by the terms of the claims rather than the description of the embodiment above and is intended to include any modifications within the scope and meaning equivalent to the terms of the claims.

REFERENCE SIGNS LIST 1 inspection apparatus; 10 housing; 12 vial; 14 wall portion; 20 UV light source; 30 conductivity meter; 32 measurement unit; 34 substrate; 50 power supply apparatus; 102 cover; 142 first surface; 144 second surface; 146, 323 opening; 148 packing; 324 electrode; 324a, 344 electrode contact; 326 thermistor; 326a, 346 thermistor contact; 327, 328 coupling portion; 342 circuit; 343 connection portion; A1 water section; A2 electric section; F flow channel; P pump; S sample water

The invention claimed is:

1. An inspection apparatus that inspects sample water, the inspection apparatus comprising:
a housing;
a wall portion that partitions a space in the housing into a first section and a second section, the wall portion being provided with an opening;
a conductivity meter that measures a conductive property of sample water; and
a flow-in tube through which sample water flows into the conductivity meter, wherein
the conductivity meter includes
a measurement unit including an electrode portion arranged as being in contact with sample water, and
a substrate on which a circuit is mounted, the circuit processing information outputted from the measurement unit,
the measurement unit and the substrate are connected to each other with the wall portion being interposed,
the measurement unit is arranged on a first surface of the wall portion on a side of the first section such that the electrode portion is located in the opening, and
the substrate is arranged on a second surface of the wall portion on a side of the second section such that a contact that electrically connects the electrode portion and the circuit to each other is located in the opening.

2. The inspection apparatus according to claim 1, further comprising a seal arranged around an outer circumference of the opening in the first surface and between the wall portion and the measurement unit.

3. The inspection apparatus according to claim 1, wherein
a contact of the electrode portion in contact with the contact of the substrate is plated with gold.

4. The inspection apparatus according to claim 1, wherein
the measurement unit further includes a temperature sensor that measures a temperature of sample water,
a contact of the temperature sensor is arranged as being located in the opening when the measurement unit is arranged on the first surface, and
the contact of the substrate that electrically connects the contact of the temperature sensor and the circuit to each other is arranged as being located in the opening when the substrate is arranged on the second surface.

5. The inspection apparatus according to claim 1, wherein
the conductivity meter further includes a connection portion that connects the measurement unit and the substrate to each other.

6. A conductivity meter that measures a conductive property of sample water, the conductivity meter comprising:
a measurement unit including an electrode portion arranged as being in contact with sample water; and
a substrate on which a circuit is mounted, the circuit processing information outputted from the measurement unit, wherein
the measurement unit and the substrate are connected to each other with a wall portion being interposed, the wall portion partitioning a space in a housing into a first section and a second section,
the measurement unit is arranged on a first surface of the wall portion on a side of the first section such that the electrode portion is located in an opening provided in the wall portion, and
the substrate is arranged on a second surface of the wall portion on a side of the second section such that a contact that electrically connects the electrode portion and the circuit to each other is located in the opening.

7. The conductivity meter according to claim 6, wherein the measurement unit is arranged on the first surface of the wall portion with a seal being interposed, the seal being arranged around an outer circumference of the opening in the first surface.

\* \* \* \* \*